(12) United States Patent
Thayer (10) Patent No.: US 7,947,020 B2
(45) Date of Patent: May 24, 2011

(54) RETRACTABLE SAFETY SYRINGE

(75) Inventor: Daniel Thayer, Mission Viejo, CA (US)

(73) Assignee: Safeshot Technologies, LLC, Mission Viejo, CA (US)

( * ) Notice: Subject to any disclaimer, the term of this patent is extended or adjusted under 35 U.S.C. 154(b) by 436 days.

(21) Appl. No.: 11/409,617

(22) Filed: Apr. 24, 2006

(65) Prior Publication Data
US 2006/0253074 A1 Nov. 9, 2006

Related U.S. Application Data

(60) Provisional application No. 60/679,113, filed on May 9, 2005.

(51) Int. Cl.
*A61M 5/32* (2006.01)
(52) U.S. Cl. .......................................... 604/195
(58) Field of Classification Search .................. 604/110, 604/195, 219
See application file for complete search history.

(56) References Cited

U.S. PATENT DOCUMENTS

| | | | |
|---|---|---|---|
| 4,766,908 A | * | 8/1988 | Clement |
| 4,838,869 A | * | 6/1989 | Allard |
| 4,950,241 A | * | 8/1990 | Ranford |
| 4,966,593 A | * | 10/1990 | Lennox |
| 5,215,015 A | * | 6/1993 | Iida |
| 5,215,533 A | * | 6/1993 | Robb |
| 5,334,155 A | * | 8/1994 | Sobel |
| 5,385,551 A | * | 1/1995 | Shaw |
| 5,389,076 A | * | 2/1995 | Shaw |
| 5,423,758 A | * | 6/1995 | Shaw |
| 5,578,011 A | * | 11/1996 | Shaw |
| 5,578,015 A | * | 11/1996 | Robb ........................... 604/195 |
| 5,601,534 A | * | 2/1997 | Turner |
| 5,632,733 A | * | 5/1997 | Shaw |
| 5,658,257 A | * | 8/1997 | Ryles |
| 5,868,713 A | * | 2/1999 | Klippenstein |
| 5,964,735 A | * | 10/1999 | Alexander |
| 5,971,964 A | * | 10/1999 | Donaldson |
| 6,033,385 A | | 3/2000 | Liu |
| 6,036,674 A | | 3/2000 | Caizza et al. |
| 6,050,977 A | | 4/2000 | Adams |
| 6,090,077 A | | 7/2000 | Shaw |
| 6,193,695 B1 | | 2/2001 | Rippstein, Jr. |

(Continued)

*Primary Examiner* — Kevin C Sirmons
*Assistant Examiner* — Deanna K Hall
(74) *Attorney, Agent, or Firm* — K&L Gates LLP; Andrew L. Reibman; Louis C. Cullman

(57) ABSTRACT

A retractable safety syringe may have a ferrule and needle which are selectively removeable from a distal end of a syringe body. In particular, the ferrule may have an annular flange. A wedge element may be frictionally engaged to the ferrule and a distal end of the syringe body. To retract the needle into the syringe body, a punch of a piston displaces the wedge element off of an annular flange of the ferrule. At about the same time, longitudinally offset tabs engage an annular flange and retract the needle into the syringe body via a retraction force created by a variable vacuum compartment or tension member.

Alternatively, the ferrule and needle may be temporarily fixed to the distal end of the syringe body via a detent and/or o-ring which engages a lower undercut groove and an upper undercut groove of the ferrule. An annular ring of the piston may have longitudinal offset tabs which engage an annular ring of the ferrule. Upon engagement, the retraction force of the variable vacuum compartment is sufficient to overcome any retaining forces created by the detent and/or the o-ring. Thereby, the needle and ferrule may be retracted into the syringe body.

The longitudinal offset tabs may cant the needle when the needle is retracted into the syringe body.

28 Claims, 8 Drawing Sheets

U.S. PATENT DOCUMENTS

| | | |
|---|---|---|
| 6,368,303 B1 | 4/2002 | Caizza |
| 6,413,236 B1 * | 7/2002 | Van Dyke ..................... 604/110 |
| 6,632,198 B2 | 10/2003 | Caizza |
| 6,840,291 B2 | 1/2005 | Caizza et al. |

* cited by examiner

RETRACTABLE SAFETY SYRINGE

CROSS-REFERENCE TO RELATED APPLICATIONS

This is a non-provisional application claiming the benefits of U.S. Provisional Patent Application Ser. No. 60/679,113, filed May 9, 2005, the entire contents of which are expressly incorporated herein by reference.

STATEMENT RE: FEDERALLY SPONSORED RESEARCH/DEVELOPMENT

Not Applicable

BACKGROUND

The present invention relates generally to retractable safety syringes which retract a needle into a syringe body after use of the safety syringe to inject medication into a patient for preventing syringe reuse and accidental needle prickings.

In recent years, the public (e.g., drug addicts, drug users, medical personnel and healthcare providers and the like) has become increasingly aware of the health hazards associated with needle reuse and accidental needle prickings. For example, at least twenty blood-borne pathogens may be transmitted by the reuse of needles or accidental needle prickings. For example, Human Immunodeficiency Virus (HIV), Acquired Immunodeficiency Syndrome (AIDS), Hepatitis B, Hepatitis C, syphilis, malaria, tuberculosis, and herpes. Despite the awareness of the risk of needle reuse and accidental needle prickings, at least 36 percent of HIV/AIDS cases and more than 50 percent of Hepatitis B and Hepatitis C cases in the United States may be linked to the sharing of needles among drug addicts. Accordingly, there is a need to curb the practice of sharing needles among drug addicts.

The problem of needle sharing or needle reuses is further amplified when viewed in relation to the world population. For example, approximately 30 percent of reported HIV/AIDS cases in Brazil, Chile, Uruguay, Paraguay and Argentina are directly related to the sharing of contaminated needles among drug addicts. Approximately 70 percent of the HIV cases reported in China are directly linked to the sharing of contaminated needles. In eastern European countries, 80 percent of injection drug addicts admit to sharing contaminated needles. Approximately 43 percent of HIV/AIDS cases reported in Poland and Yugoslavia are linked to the sharing of contaminated needles among drug addicts.

Accidental needle prickings also pose a threat to healthcare workers. In particular, approximately one million accidental needle prickings are reported by healthcare workers annually. However, it is believed that at least three million accidental needle prickings occur each year, of which about two million are unreported. Various studies estimate that out of all the accidental needle pricking injuries that occur to nurses, approximately 40 percent to 53 percent go unreported. Various studies also estimate that out of all the needle pricking injuries that occur to laboratory technicians, approximately 92 percent go unreported. Various studies further estimate that out of all the needle pricking injuries that occur to physicians, approximately 70 percent to 95 percent go unreported.

In 1997, the Center for Disease Control and Prevention (CDC) sponsored a study which found that approximately 76 percent of needle pricking injuries could be avoided by using safety needles. Presently, there are at least 250 types of safety syringes. Unfortunately, the safety syringes that currently exist have been criticized for various problems associated in operating the safety syringe and its ineffectiveness.

Accordingly, there is a need in the art for an improved safety syringe.

BRIEF SUMMARY

Three embodiments of a retractable safety syringe are disclosed herein and address the problems identified above, below and those that are known in the art.

In a first embodiment of the safety syringe, the same may have a plurality of adapters which are each selectively removeable from a distal end of the safety syringe. Each of the adapters may be attached to a respective one of a plurality of different sized needles. In this manner, any one of the plurality of needles may be attached to the syringe body of the retractable safety syringe via the adapter. Also, needles of different sizes may be selectively attached to the syringe body depending upon the required or suggested needle size based on the medication to be administered. The ferrule (i.e., needle holder) and needle are attached to the adapter via a wedge element. In particular, the wedge element is frictionally engaged to an outer surface of an annular flange of the ferrule and an inner surface of a first step of the adapter. To disengage the ferrule from the adapter, a punch of a plunger displaces the wedge element off of the annular flange and about a landing of the ferrule. At this point, the ferrule may slide out of the adapter and into the syringe body. When the punch displaces the wedge element off of the annular flange, longitudinal offset tabs also engage the annular flange. A retraction force of a variable vacuum compartment then withdraws the piston, ferrule and needle into the syringe body. The longitudinal offset tabs also cant the needle against an inner surface of the syringe body thereby preventing needle reuse and accidental needle prickings.

The first embodiment of the retractable safety syringe may also be equipped with a braking mechanism to aid in the operation of the safety syringe while filling the variable fluid chamber with medication and injecting the medication into the patient.

A second embodiment of the retractable safety syringe is similar to the first embodiment except that the second embodiment of the safety syringe does not have an adapter. The wedge element is frictionally engaged to the outer surface of the annular flange and an inner surface of the syringe body. The piston is formed with a punch which displaces the wedge element off of the annular flange and about the landing. Also, the piston is formed with distally protruding annular ring with longitudinal offset tabs formed on an inner periphery thereof. When the piston is extended to the fully extended position, the longitudinal offset tabs engage a proximally protruding annular ring of the ferrule. Since at the fully extended position, the punch also displaces the wedge element off of the annular flange, the retraction force of the variable vacuum compartment then retracts the piston, ferrule and needle into the syringe body.

The second embodiment of the safety syringe may also have a braking mechanism.

A third embodiment of the safety syringe may be similar to the second embodiment of the safety syringe. The ferrule of the third embodiment is temporarily fixed to the distal end of the syringe body via a detent and/or an o-ring instead of the wedge element. The detent is received into a lower undercut groove of the ferrule. The o-ring is received into an upper undercut groove of the ferrule. The o-ring frictionally engages the inner surface of the syringe body and the detent frictionally engages the lower undercut groove. These frictional forces prevent retraction of the ferrule and needle into the syringe body when the needle is being pierced into the medication container for filling medication into the variable fluid chamber and the skin of the patient for injecting the medication into the patient.

To retract the ferrule and needle into the syringe body, the piston is traversed to the fully extended position. Upon which, the longitudinal offset tabs engage an annular ring of the ferrule. The retraction force of the variable vacuum compartment is able to overcome the frictional forces caused by the detent and the o-ring to thereby retract the needle and ferrule into the syringe body. The third embodiment of the safety syringe may also have a braking mechanism.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
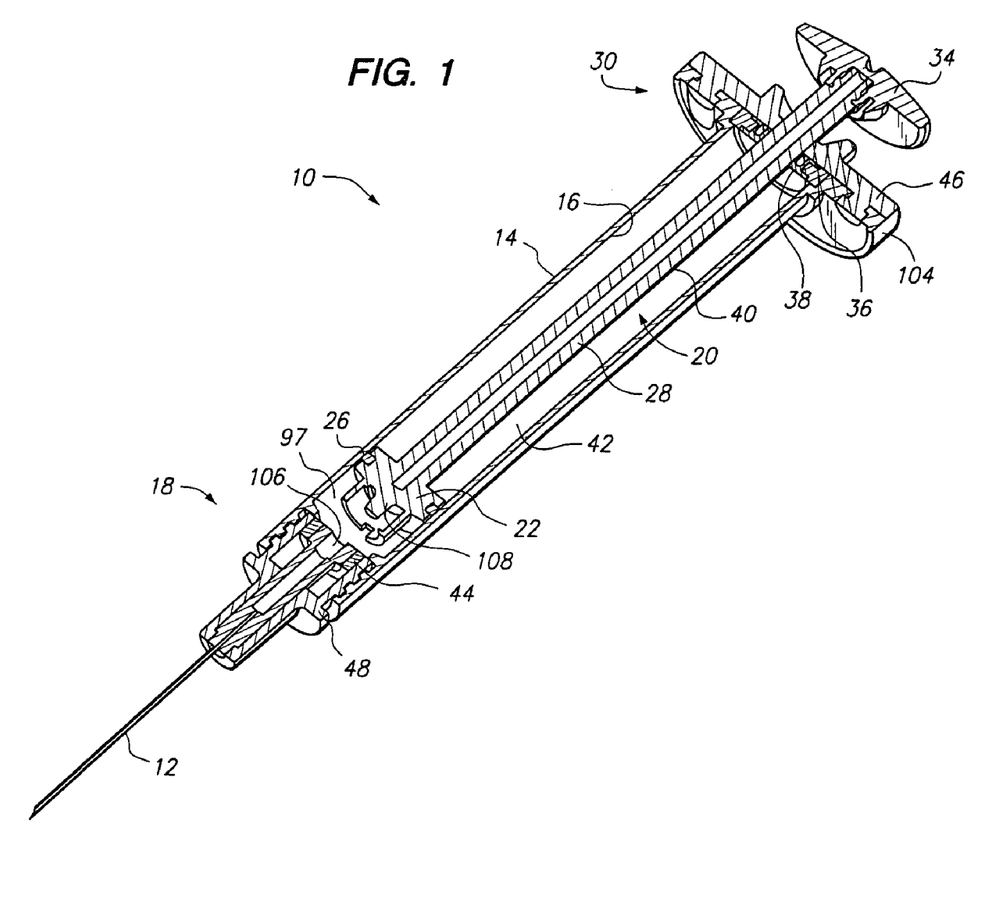
FIG. 1 is a cross sectional perspective view of a first embodiment of a safety syringe.

Referring now to the drawings, which are for the purposes of illustrating the preferred embodiments of the safety syringe and not for the purpose of limiting the same, FIG. 1 is a perspective view of the safety syringe in accordance with a first embodiment. The safety syringe 10 of the first embodiment prevents needle reuse and accidental needle prickings with contaminated syringe needles.

The safety syringe 10 prevents syringe reuse and accidental needle prickings by retracting a needle 12 of the syringe into a body 14 of the syringe after the needle 12 has been used to administer a medication to a patient. The needle 12 once retracted within the syringe body 14 (see FIG. 4) is prevented from exiting the syringe body 14 or is retained positively within the syringe body 14 because the needle 12 is canted against an inner surface 16 of the syringe body 14. In this manner, the needle 12 is prevented from escaping out of the distal end 18 of the syringe body 14 such that the syringe 10 is incapable of being reused and the needle 12 is inaccessible thereby preventing accidental needle prickings.

The syringe 10 may include a plunger 20 which is axially traversable within the syringe body 14. The plunger 20 may have a piston 22 disposed on its distal end with a first sealing ring 26 providing an airtight and fluidtight interface between the piston 22 and the inner surface 16 of the body 14. A rigid shaft 28 may be attached to the piston 22 and protrude out a proximal end 30 of the body 14. A proximal end of the shaft 28 may have a thumb platform 34 attached thereto. The thumb platform 34 provides an area for the user to press to traverse the piston 22 from a retracted position to an extended position (first extended position), and a fully extended position (second extended position). The user may also pull on the thumb platform 34 to traverse the piston 22 from the extended position (first extended position) or the fully extended position (second extended position) to the retracted position. The proximal end 30 of the body 14 may have an attachment base 36 attached thereto. A second sealing ring 38 may be attached to the attachment base 36 and provide an airtight and fluidtight seal between the attachment base 36 and the outer surface 40 of the rigid shaft 28. The volume of space between the first sealing ring 26 disposed on the piston 22 and the second sealing ring 38 disposed on the attachment base 36 defines a variable vacuum compartment 42.

Generally, in relation to the first embodiment of the syringe, the retracted position is when the piston 22 is closer to the proximal end of the body 14 compared to the distal end of the body. But, the retracted position may include the situation when the piston 22 does not contact the ferrule 74 and the piston is closer to the distal end of the body 14 compared to the proximal end of the body 14. The extended position (first extended position) is when the piston 22 contacts the ferrule 74 or is closely adjacent to the ferrule 74 but does not engage the ferrule 74 or displace the wedge element 44 off of an annular flange 76. The fully extended position (second extended position) is when the piston 22 contacts the ferrule 74 and does engage the ferrule 74. Also, at the fully extended position (second extended position), the wedge element 44 is displaced off of the annular flange 76 and about the landing 78.

The variable vacuum compartment 42 produces a retraction force which is used to withdraw the needle 12 into the syringe body 14. Initially, the syringe 10 is provided to a user (e.g., medical professional) with the piston 22 in the retracted position. As the medical professional fills the syringe 10 with a medication and injects the medication into the patient, the piston 22 is traversed between the retracted position, the extended position (i.e., first extended position), and a fully extended position (i.e., second extended position). At the retracted position, the variable vacuum compartment 42 may have a pressure equal to the ambient or atmospheric pressure. As the piston 22 is traversed from the retracted position to the extended position (first extended position) and the fully extended position (second extended position), the variable vacuum compartment 42 has a negative pressure compared to the atmospheric pressure. The reason is that additional air molecules are not introduced into the variable vacuum compartment 42 even though the variable vacuum compartment 42 has an increase in volume due to the traversal of the piston 22 from the retracted position to the extended position (first extended position). At the fully extended position (second extended position), the retraction force created by the negative pressure within the variable vacuum compartment 42 is sufficient to withdraw the needle 12 into the syringe body 14 but for a wedge element 44 and a braking mechanism 46, which will be discussed further below.

The distal end 18 of the syringe body 14 may be selectively engageable to any one of a plurality of adapters 48. Each adapter 48 may have a different size or type of needle. The adapter 48 permits the medical professional to select the appropriate size needle for the medication to be administered. For example, if the medication requires a shorter needle, the medical professional may attach an adapter 48 with a short needle to the syringe body 14. Alternatively, if the medication to be administered requires a longer needle, the medical professional may attach an adapter 48 with a longer needle to the syringe body 14.

Figure 2:
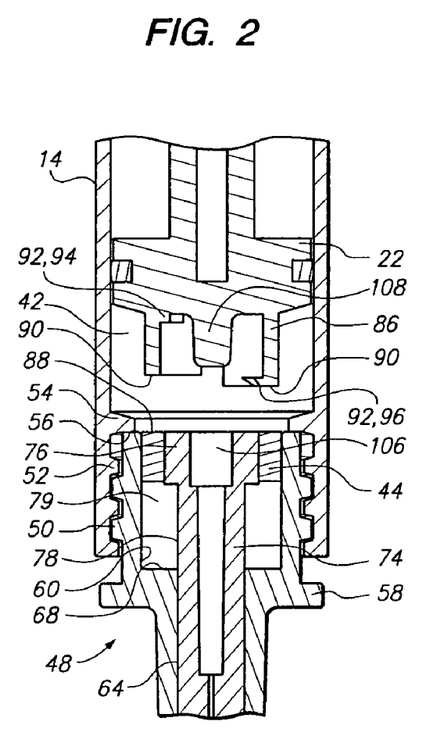
FIG. 2 is an enlarged cross-sectional view of the safety syringe of the first embodiment illustrating a wedge element frictionally engaged to an adapter and an annular flange of a ferrule.

As shown in FIG. 2, the adapter 48 may have an outer surface with threads 50 formed thereon. These threads 50 are threadably engageable to internal threads 52 formed on the distal end 18 of the syringe body 14. In this manner, the adapter 48 may be threaded onto (i.e., engaged) or threaded off (i.e., disengaged) of the syringe body 14.

The insertion distance of the adapter 48 into the distal end 18 of the syringe body 14 may be controlled by a sprag 54 or protrusion formed about the inner surface of the syringe body 14. The sprag 54 may protrude inwardly into the syringe body 14 and provide interference such that the proximal end 56 of the adapter 48 contacts the sprag 54 to prevent further insertion of the adapter 48 into the distal end 18 of the syringe body 14. Alternatively, the insertion distance of the adapter 48 may be controlled via a flange 58 or collar of the adapter 48 which engages or contacts the distal surface of the syringe body 14 to control the insertion distance of the adapter 48 into the syringe body 14.

The inner surface of the adapter 48 may have a stair-stepped configuration. The stair-stepped configuration may have two different diameters. A first step 60 is at the proximal portion of the adapter 48. A second step 64 is located at the distal portion of the adapter 48. A riser 68 is located perpendicular to the first and second steps 60, 64 and interposed therebetween. The stair-stepped configuration of the inner surface of the adapter 48 mates with a corresponding stair-step configuration of an outer surface of a ferrule (i.e., needle holder) 74. The ferrule 74 may have an annular flange 76 which is disposable within the first step 60 of the adapter 48. The outer diameter of the annular flange 76 is less than the inner diameter of the first step 60 of the adapter 48. The wedge element 44 is frictionally engaged or disposed between the annular flange 76 and the adapter first step 60 to frictionally hold the ferrule 74 to the adapter 48. In this manner, when inserting the needle 12 into the patient's skin or medication container, the ferrule 74 as well as the needle 12 do not retract into the syringe body 14 due to the axial force on the needle 12 created by the skin of the patient or container.

Below the annular flange 76 is a landing 78 having a smaller or reduced outer diameter compared to the outer diameter of the annular flange 76. Since the length of the annular flange 76 is less than the length of the first step 60 of the adapter 48, the ferrule 74 and the adapter 48 provide a volume 79 in which the wedge element 44 may be traversed into to release the ferrule 74 from the adapter 48, as will be discussed further below. A distal portion of the ferrule 74 may have a sliding fit with the second step 64 of the adapter 48. In this manner, but for the frictional engagement of the wedge element 44 with the adapter 48 and the ferrule 74, the ferrule 74 would slide out of the adapter 48 toward the proximal end 30 of the syringe body 14. The ferrule 74 may be temporarily fixed to the adapter 48 such that the ferrule 74 cannot retract into the syringe body 14 and the ferrule 74 cannot traverse outwardly from the distal end of the adapter 48. Also, the ferrule 74 is selectively retractable into the syringe body 14 by displacing the wedge element 44 off of the annular flange 76 and about the landing 78 of the ferrule 74.

Figure 3:
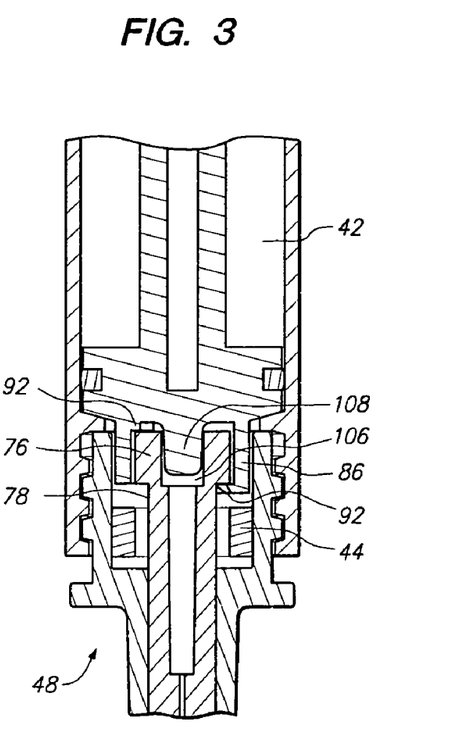
FIG. 3 is an enlarged cross sectional view of the safety syringe of the first embodiment illustrating a punch displacing the wedge element off of the annular flange and longitudinal offset tabs engaging the annular flange.

To displace the wedge element 44 about the reduced diameter landing 78 of the ferrule 74, a punch 86, which may be attached to the distal end of the piston 22, may have an annular configuration which matches or corresponds to a top surface 88 of the wedge element 44. When the piston 22 is traversed to the extended position (first extended position), the punch bottom surface 90 mates with the wedge element top surface 88. When the piston 22 is traversed to the fully extended position ((second extended position; see FIG. 3), the punch 86 pushes the wedge element 44 off of the annular flange 76 and about the landing 78. At this point, the ferrule 74 has a sliding fit with the adapter 48 and is not fixedly engaged to the adapter 48. The ferrule 74 can slide or retract into the syringe body 14.

To retract the ferrule 74 into the syringe body 14, the punch 86 is formed with longitudinal offset tabs 92 which engage the annular flange 76 of the ferrule 74 to retract the ferrule 74 into the syringe body 14. The longitudinal offset tabs 92 may engage the annular flange 76 before or after the wedge element 44 is displaced off of the annular flange 76 and about the landing 78. Upon engagement between the longitudinal offset tabs 92 and the annular flange 76, a retraction force of the variable vacuum compartment 42 traverses the piston 22 as well as the ferrule 74 and needle 12 to the retraction position thereby disposing the needle 12 within the syringe body 14 (see FIG. 4).

As shown in FIG. 2, the longitudinal offset tabs 92 may comprise an upper proximal block tab 94 and a lower distal wedge tab 96. The vertical distance between the upper proximal block tab 94 and the lower distal wedge tab 96 may be slightly smaller than a vertical length of the annular flange 76 such that the longitudinal offset tabs 92 provide a rotational force on the ferrule 74 as well as the needle 12. This rotational force cants the needle 12 once the ferrule 74 and needle 12 is within the syringe body 14 (see FIG. 4). In particular, as the punch 86 displaces the wedge element 44 about the reduced diameter, the lower distal wedge tab 96 engages a bottom surface of the annular flange 100. The upper proximal block tab 94 pushes down on a top surface of the annular flange 102, which in conjunction with the upward force created by the lower distal wedge tab 96, produces the rotational force canting the needle 12 once the needle 12 is within the syringe body 14. Once the lower distal wedge tab 96 engages the bottom surface of the annular flange 100, the retraction force traverses the piston 22, ferrule 74 and needle 12 into the syringe body 14. The upper and lower tabs 94, 96 produce a rotational force canting the needle against the inner surface of the syringe body 14. Since the needle 12 is canted and laid against an inner surface of the syringe body 14 (see FIG. 4), the needle 12 is positively retained within the syringe body 14 to prevent syringe reuse and accidental needle prickings.

Optionally, the syringe 10 may have a braking mechanism 46 which acts against the retraction force created by the variable vacuum compartment 42. The braking mechanism 46 is further explained in U.S. Provisional Patent Application Ser. No. 60/679,113 the entire contents of which are expressly incorporated herein by reference. As shown in FIG. 1, the braking mechanism 46 may be disposed about the proximal end 30 of the syringe body 14. The braking mechanism 46 may apply a frictional force against the rigid shaft 28 of the plunger 20. The frictional force may be sufficient to overcome the retraction force of the variable vacuum compartment 42 throughout the entire range between the retracted position and the extended position (first extended position). The braking mechanism 46 aids the user when filling a variable fluid chamber 97 with medication and during the injecting step when administering a medication to the patient. For example, as stated above, the syringe 10 is provided to the medical professional or user with the piston 22 in the retracted position. To fill the variable fluid chamber 97 with medication, the medical professional must depress the thumb platform 34 such that the piston 22 is traversed to the extended position (first extended position). Unfortunately, at the extended position (first extended position), the variable vacuum compartment 42 produces a retraction force to urge the piston 22 toward the retraction position. Without the braking mechanism 46, the user must provide constant pressure on the thumb platform 34 as the user pierces a medication container then slowly release the thumb platform 34 by balancing the pressure applied to the thumb platform 34 by the user's thumb and the retraction force. Fortunately, the braking mechanism 46 provides a frictional force which is sufficient to hold the piston 22 in place even though the user does not press the thumb platform 34. In this manner, to fill the variable fluid chamber 97, the user may traverse the piston 22 from the retracted position to the extended position (first extended position) by pushing on the thumb platform 34, (optional) release the thumb platform 34, pierce the medication container with the needle 12 and pull the thumb platform 34 and push finger platforms 104 to traverse the piston 22 from the extended position (first extended position) to the retracted position.

With the medication within the variable fluid chamber 97, the user may point the needle 12 upward and slightly depress the thumb platform 34 to remove any air within the variable fluid chamber 97. The braking mechanism 46 holds the piston 22 in place despite the retraction force urging the piston 22 toward the retraction position which would reintroduce air into the variable fluid chamber 42.

The user or medical professional may then pierce the patient's skin and inject the medication into the patient by depressing the thumb platform 34 and traversing the piston 22 from the retracted position to the extended position (first extended position). As the piston 22 reaches the fully extended position (second extended position; see FIGS. 3 and 4), the punch 86 displaces the wedge element 44 off of the annular flange 76 and about the landing 78. Simultaneously, or at about the same time, the lower distal wedge tab 96 engages the bottom surface of the annular flange 76 and the thumb platform 34 disengages the braking mechanism 46 from the rigid shaft 28 of the plunger 20. With the braking mechanism 46 disengaged, the wedge element 44 off of the annular flange 76, and the lower distal wedge tab 96 engaged to the annular flange 76, the retraction force retracts the needle 12 and the ferrule 74 into the syringe body 14. When the needle 12 is retracted into the syringe body 14, the upper proximal block tab 94 pushes down on the annular flange 76 while the lower distal wedge tab 96 pulls up on the annular flange 76 to cant the needle 12 within the syringe body 14.

Figure 4:
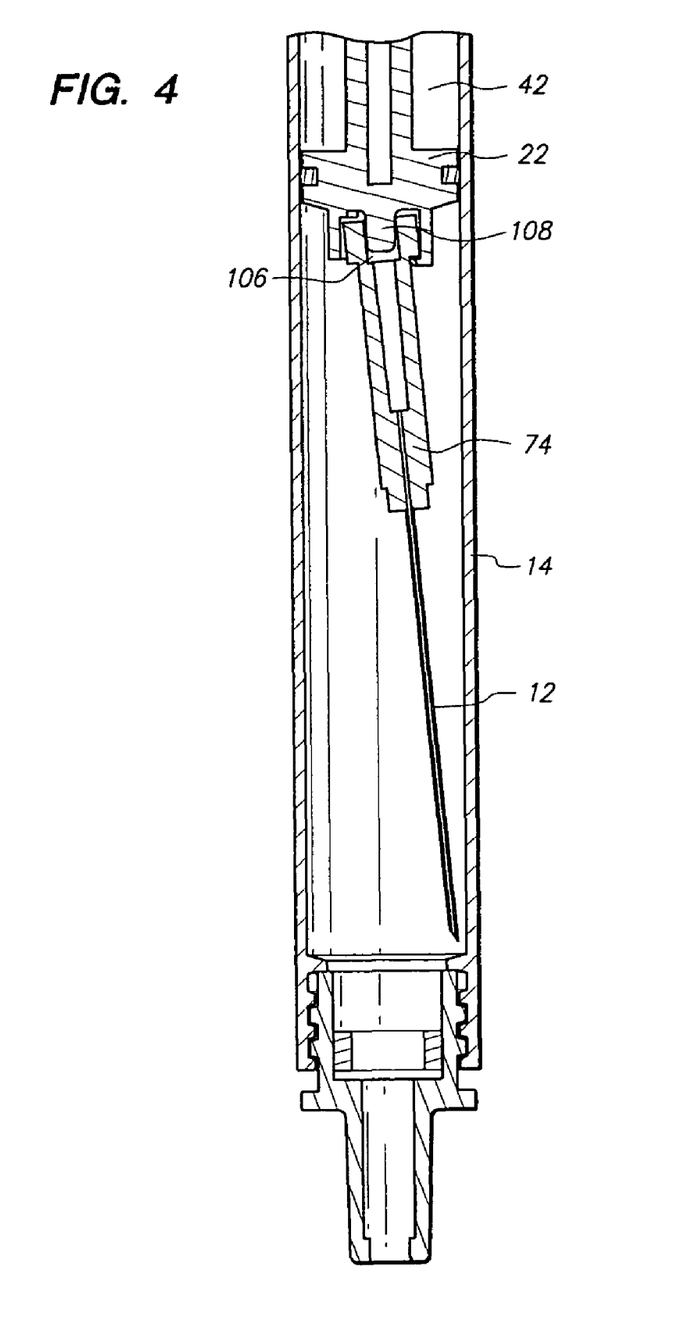
FIG. 4 is a front cross sectional view of the safety syringe of FIG. 1 wherein a needle is retracted into a body of the syringe and canted to one side.

In the first embodiment of the safety syringe 10, the ferrule 74 may have a protuberance 108. The protuberance 108 may mate with a corresponding recess 106 of the ferrule 74. In this manner, when the piston 22 is traversed to the fully extended position (second extended position; see FIG. 3), the corresponding protuberance 108 and recess 106 eject as much of the fluid from the variable fluid chamber 42 as possible. More particularly, the recess 106 of the ferrule 74 may have a cylindrical configuration. The length of the recess 106 may be about equal to the length of the annular flange 76. The protuberance 108 may be formed on a distal end of the piston 22 and aligned to the recess 106. The protuberance 108 may be flexible such that the needle 12 may be canted to one side when withdrawn inside the syringe body 14, as shown in FIG. 4.

Figure 5:
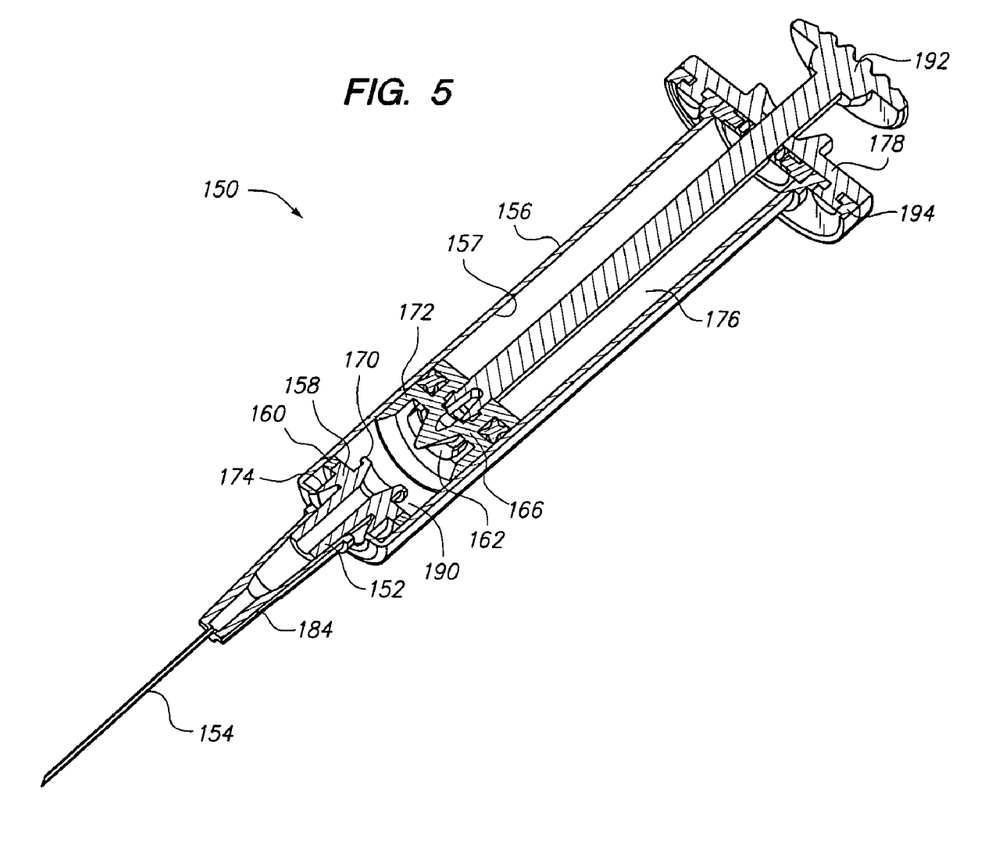
FIG. 5 is a cross sectional perspective view of a second embodiment of a safety syringe.
Figure 6:
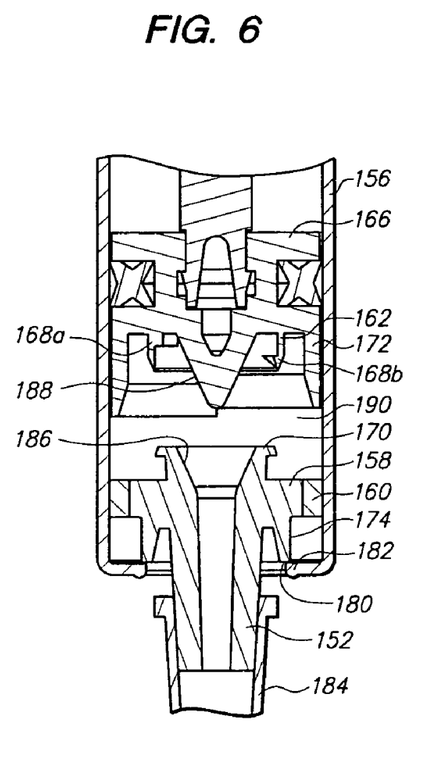
FIG. 6 is an enlarged cross sectional view of the safety syringe of the second embodiment illustrating a wedge element frictionally engaged to a body of the syringe and an annular flange of a ferrule.
Figure 7:
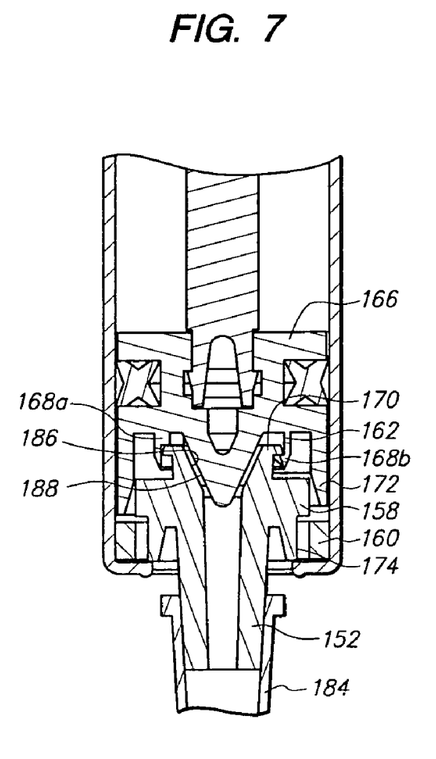
FIG. 7 is an enlarged cross sectional view of the safety syringe of the second embodiment illustrating a punch displacing the wedge element off of the annular flange and longitudinal offset tabs engaging an annular ring.

Referring now to FIGS. 5-7, a second embodiment of the safety syringe 150 is shown for the purpose of illustration and not limitation. The second embodiment of the safety syringe 150 is different from the first embodiment in that the ferrule (i.e., needle holder) 152 and needle 154 are not selectively removeable from the syringe body 156 via an adapter 48. Rather, the ferrule 152 and the needle 154 are intimately associated with the syringe body 156.

The ferrule 152 of the second embodiment may also have an annular flange 158. A wedge element 160 may be frictionally engaged between the outer surface of the annular flange 158 and the inner surface 157 of the syringe body 156. The frictional engagement therebetween prevents the ferrule 152 and the needle 154 from being retracted into the syringe body 156 as the needle pierces the skin of the patient to administer the medication or as the needle 154 pierces the medication container to fill the variable fluid chamber 190 with medication.

A distally protruding annular ring 162 may be attached to the distal end of the piston 166. The annular ring 162 may have longitudinally offset tabs 168a, 168b (see FIGS. 6 and 7) disposed about an inner periphery of the annular ring 162. The longitudinal offset tabs 168a, 168b may comprise an upper proximal block tab 168a and a lower distal wedge tab 168b, as shown in FIGS. 6 and 7. The longitudinally offset tabs 168a, 168b (see FIGS. 6 and 7) may engage an annular ring 170 disposed adjacent the proximal end of the ferrule 152. The second embodiment of the safety syringe 10 is different than the first embodiment of the safety syringe 10 in that the longitudinal offset tabs 168a, 168b engage the annular ring 170 of the ferrule 152 instead of the annular flange 76 of the ferrule 74. Alternatively, it is contemplated that the punch 172 of the piston 166 in the second embodiment of the safety syringe 150 may be formed with longitudinal offset tabs 168a, 168b to engage the annular flange 158 when the wedge element 160 is displaced off of the annular flange 158 and onto the landing 174 of the ferrule 152. Upon engagement of the longitudinal offset tabs 168 with the annular ring 170 or annular flange 158 of the ferrule, the ferrule 152 and needle 154 are retracted into the syringe body 156 via the retraction force of the variable vacuum compartment 176.

The second embodiment of the safety syringe 150 may also have a braking mechanism 178 (see FIG. 5) which behaves in the same manner as the braking mechanism 46 discussed in relation to the first embodiment of the safety syringe 10 and disclosed in U.S. Provisional Patent application Ser. No. 60/679,113, the entire contents of which are expressly incorporated herein by reference.

Referring now to FIG. 6, the landing 174 of the ferrule 152 may have a distal surface 180 which engages an inwardly directed flange 182 at the distal end of the syringe body 156. This prevents the ferrule 152 and needle 154 from being pushed out of the syringe body 156 when the punch 172 displaces the wedge element 160 off of the annular flange 158 and about the landing 174.

Optionally, the second embodiment of the safety syringe 150 may have a coupling 184 which attaches the needle 154 to the ferrule 152.

The second embodiment of the safety syringe 150 may also have a ferrule 152 having a proximally facing frusto conical surface 186, as shown in FIG. 6. This surface 186 may mate with a corresponding distally facing frusto conical surface 188 of the piston 166. In this manner, when the piston 166 is traversed to the fully extended position (second extended position; see FIG. 7), the corresponding surfaces 186, 188 eject as much of the fluid from the variable fluid chamber 190 as possible. Similar to the first embodiment of the safety syringe 10, the piston 166 of the second embodiment of the safety syringe 150 may be traversed between the retracted position, the extended position (first extended position) and the fully extended position (second extended position). The retracted position, the extended position (first extended position) and the fully extended position (second extended position) of the piston 166 for the second embodiment of the safety syringe 150 may have an identical meaning compared to the first embodiment of the safety syringe 10.

The operation of the second embodiment of the safety syringe 150 may have a similar operation as the first embodiment of the safety syringe 10. In use, the second embodiment of the safety syringe 150 may be provided to the user or medical professional with the piston 166 in the retracted position (i.e., piston 166 located at proximal end of body 156). To fill the variable fluid chamber 190 with medication, the user will traverse the piston 166 from the retracted position to the extended position (first extended position) by pressing the thumb platform 192. Once the piston 166 is traversed to the extended position (first extended position), the user may release the thumb platform 192. Fortunately, the braking mechanism 178 overcomes or equals the retraction force created by the variable vacuum compartment 176 to hold the piston 166 in position. The user may then pierce the medication container with the needle 154 of the syringe 150 and retract the piston 166 to the retracted position by pulling the thumb platform 192 and pushing on finger platform 194. Such traversal fills the variable fluid chamber 190 with the medication.

With the medication within the variable fluid chamber 190, the user may point the needle 154 upward and slightly depress the thumb platform 192 to remove any residual air within the variable fluid chamber 190. The braking mechanism 178 holds the piston 166 in place despite the retraction force urging the piston 166 toward the retraction position which would reintroduce air into the variable fluid chamber 190.

The user may then pierce the patient's skin with the needle 154. The needle 154 and ferrule 152 is prevented from being retracted into the syringe body 156 due to the frictional force of the wedge element 160 on the inner surface 157 of the syringe body 156 and the outer surface of the annular flange 158. The user then depresses the thumb platform 192 to traverse the piston 166 from the retracted position to the extended position (first extended position) thereby injecting the medication into the patient. When the piston 166 is further traversed to the fully extended position (second extended position), the distally facing frusto conical surface 188 of the piston 166 mates with the proximally facing frusto conical surface 186 of the ferrule 152 such that as much of the fluid from the variable fluid chamber 190 is injected into the patient. Also, the punch 172 of the piston 166 displaces the wedge element 160 off of the annular flange 158 and about the landing 174. Additionally, the braking mechanism 178 releases the rigid shaft of the plunger. At this point, the retraction force created by the variable vacuum compartment 176 slides the ferrule 152 and needle 154 to the retracted position. Also, the longitudinal offset tabs 168a, 168b engage the annular ring 170 of the ferrule 152. When the needle 154 is retracted into the syringe body 156, the upper proximal block tab 168a pushes down on the annular ring 170 and the lower distal wedge tab 168b pulls up on the annular ring 170 to cant the needle to one side of the syringe body 156 to prevent needle reuse and accidental needle prickings.

Figure 8:
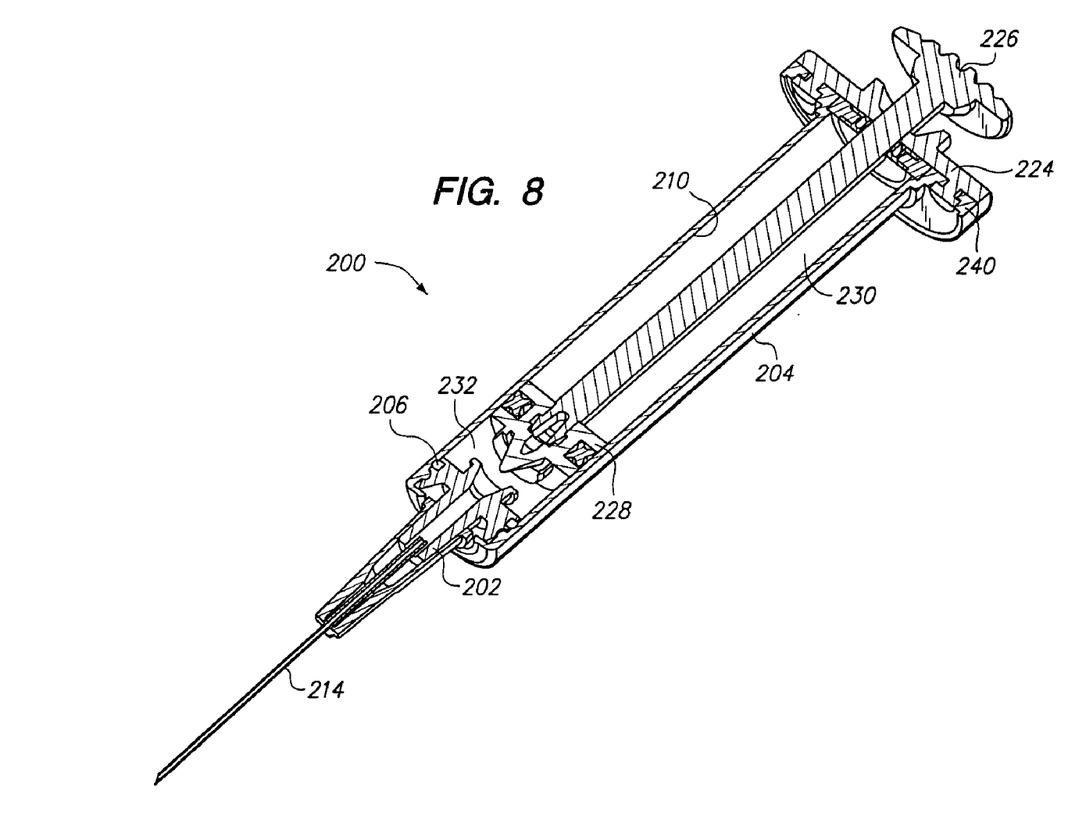
FIG. 8 is a cross sectional perspective view of a third embodiment of a safety syringe.
Figure 9:
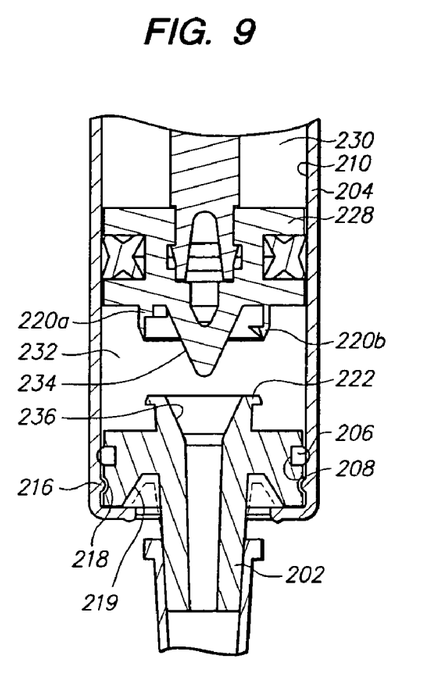
FIG. 9 is an enlarged cross sectional view of the safety syringe of the third embodiment illustrating a detent formed in a body of the syringe removeably engaged to a lower undercut groove formed in a ferrule.
Figure 10:
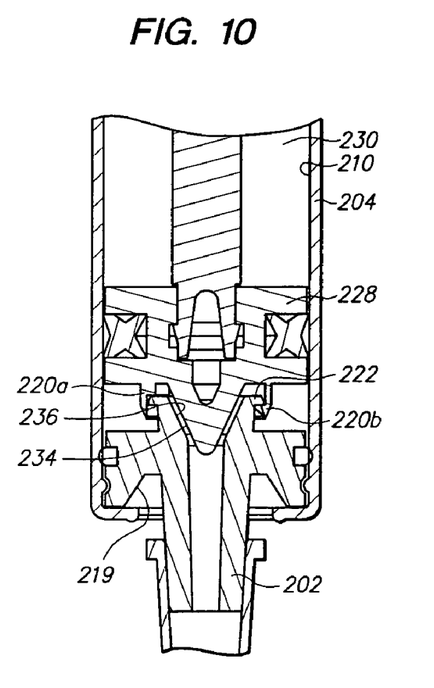
FIG. 10 is an enlarged cross sectional view of the safety syringe of the third embodiment illustrating longitudinal offset tabs engaged to an annular ring.

Referring now to FIGS. 8-10, a third embodiment of the safety syringe 200 is shown. The third embodiment of the safety syringe 200 is similar to the second embodiment except that the ferrule (i.e., needle holder) 202 is temporarily fixed to the syringe body 204. As shown in FIG. 9, the ferrule 202 may have an upper undercut groove 208 which is sized and configured to receive the o-ring 206. The o-ring 206 when received into the upper undercut groove 208 protrudes slightly beyond the outer periphery of the undercut groove 208 and engages the inner surface 210 of the syringe body 204. The pressure on the inner surface 210 of the syringe body 204 created by the o-ring 206 creates a fluid tight seal between the ferrule 202 and the syringe body 204.

The inner surface 210 of the syringe body 212 at its distal end may have a detent 216 (see FIG. 9) which engages a lower undercut groove 218 of the ferrule 202. The engagement between the detent 216 and the lower undercut groove 218 may provide stability or a retaining force such that the ferrule 202 is retained to the distal end of the syringe body 204 during injection of the medication into the patient and filling of the medication into a variable fluid chamber. The retaining force may be varied by the size of the detent 216 and the lower undercut groove 218. Additionally or alternatively, the retaining force may be varied by providing more or less flex to a V shaped configuration 219. If the V shaped configuration 219 is made more flexible then the retaining force is reduced. In contrast, if the V shaped configuration 219 is made less flexible (i.e., rigid) then the retaining force is increased. By way of example and not limitation, as shown in FIG. 9, more material may be added to the ferrule as shown by the dashed lines to rigidize the V shaped configuration. The magnitude of the retaining force may be set lower than a retraction force of a variable vacuum compartment 230.

Upon engagement of the longitudinal offset tabs 220a, 220b (see FIG. 9) with the annular ring 222 of the ferrule 202 (see FIG. 10), the retraction force may overcome the retaining force provided by the detent 216 such that the ferrule 202 and the needle 214 are retracted into the syringe body 204. When the ferrule and needle are retracted into the body 204, the upper proximal block tab 220a pushes down on the annular ring and the lower distal wedge tab 220b pulls up on the annular ring canting the needle to one side.

Alternatively or additionally, the o-ring 206 may frictionally engage the inner surface of the syringe body 204 to temporarily fix the ferrule 202 to the distal end of the syringe body 204 such that the needle 214 and ferrule 202 do not retract into the syringe body 204 upon administration of the medication to the patient, and more particularly, when the needle 214 pierces the skin of the patient or when the needle 214 pierces the medication container. In this regard, when the longitudinal offset tabs 220a, b engage the annular ring 222, the retraction force overcomes the friction force of the o-ring and the retaining force such that the needle 214 and ferrule 202 are retracted into the syringe body 204. As the ferrule 202 is retracted into the syringe body 204, the o-ring may be displaced out of the upper undercut groove 208 and may be lodged into the lower undercut groove 218. The o-ring 206 may reduce the pressure it 206 applies to the inner surface 210 of the syringe body 204 when lodged in the lower undercut groove 218. As such, the ferrule 202 is permitted to slide toward the proximal end of the syringe body 204 and retract into the syringe body 204.

Optionally the third embodiment of the safety syringe 200 may also have a braking mechanism 224 discussed in relation to the first embodiment of the safety syringe and disclosed in U.S. Prov. Pat. Application Ser. No. 60/679,113, the entire contents of which are expressly incorporated herein by reference.

As a preliminary matter, the piston 228 of the third embodiment of the safety syringe 200 may be traversed between a retracted position, extended position (first extended position) and a fully extended position (second extended position). Generally, the retracted position is when the piston 228 is closer to the proximal end of the body 204 compared to the distal end of the body 204. But, the retracted position may include the situation when the piston 228 does not contact the ferrule 202 and the piston 228 is closer to the distal end of the body 204 compared to the proximal end of the body. The extended position (first extended position) is when the piston 228 contacts the ferrule 202 or is closely adjacent to the ferrule 202 but does not engage the ferrule 202. The fully extended position (second extended position) is when the piston 228 contacts the ferrule 202 and does engage the ferrule 202. Also, at the fully extended position (second extended position), the longitudinal offset tabs 220 have engaged the annular ring 222 of the ferrule 202.

The operation of the third embodiment of the safety syringe 200 may be similar to the operation of the second embodiment of the safety syringe 150. For example, the third embodiment of the safety syringe 200 is provided to a user or medical professional with the piston 228 in a retracted position. The user then depresses the thumb platform 226 to traverse the piston 228 from the retracted position to the extended position (first extended position). The braking mechanism 224 prevents the piston 228 from being traversed back to the retracted position due to the retraction force of the variable vacuum compartment 230. The user then inserts the needle 214 into a medication container and traverses the piston 228 from the extended position (first extended position) to the retracted position by pulling on the thumb platform 226 and pushing on finger platform 240. This fills the variable fluid chamber 232 with the medication. The user than inverts the syringe 200 to eject any residual air from within the variable fluid chamber 232 by slightly pressing on the thumb platform 226. Without the braking mechanism 224, the piston 228 would be retracted back to the retracted position and air would be reintroduced into the variable fluid chamber 232. Fortunately, the braking mechanism 224 prevents such retraction.

The user then pierces the patient's skin with the needle 214 and injects the medication into the patient by traversing the piston 228 from the retracted position to the extended position (first extended position) and further to the fully extended position (second extended position; see FIG. 10). At the fully extended position (second extended position), a distally facing frusto conical surface 234 of the piston 228 mates with a proximally facing frusto conical surface 236 of the ferrule 202. This injects as much of the medication into the patient as possible. The longitudinal offset tabs 220a, 220b (see FIG. 10) also engage the annular ring 222 of the ferrule 202 and the braking mechanism 224 is disengaged. The retraction force now releases the detent 216 from the lower undercut groove 218 and urges the needle 214 and the ferrule 202 as well as the piston 228 into the syringe body 204. Once the needle 214 is retracted into the body 204, the longitudinal offset tabs 220a, 220b cant the needle 214 against the inner surface 210 of the syringe body 204 to prevent needle reuse and accidental needle prickings.

In an aspect of the safety syringes 10, 150, 200 of the first through third embodiments, the retraction force may be spring induced instead of vacuum induced. The spring induced retraction force will be discussed in relation to the third embodiment of the safety syringe 200 but the various aspects of the spring induced retraction force may be employed in the first and second embodiments of the safety syringe 10, 150.

Figure 11:
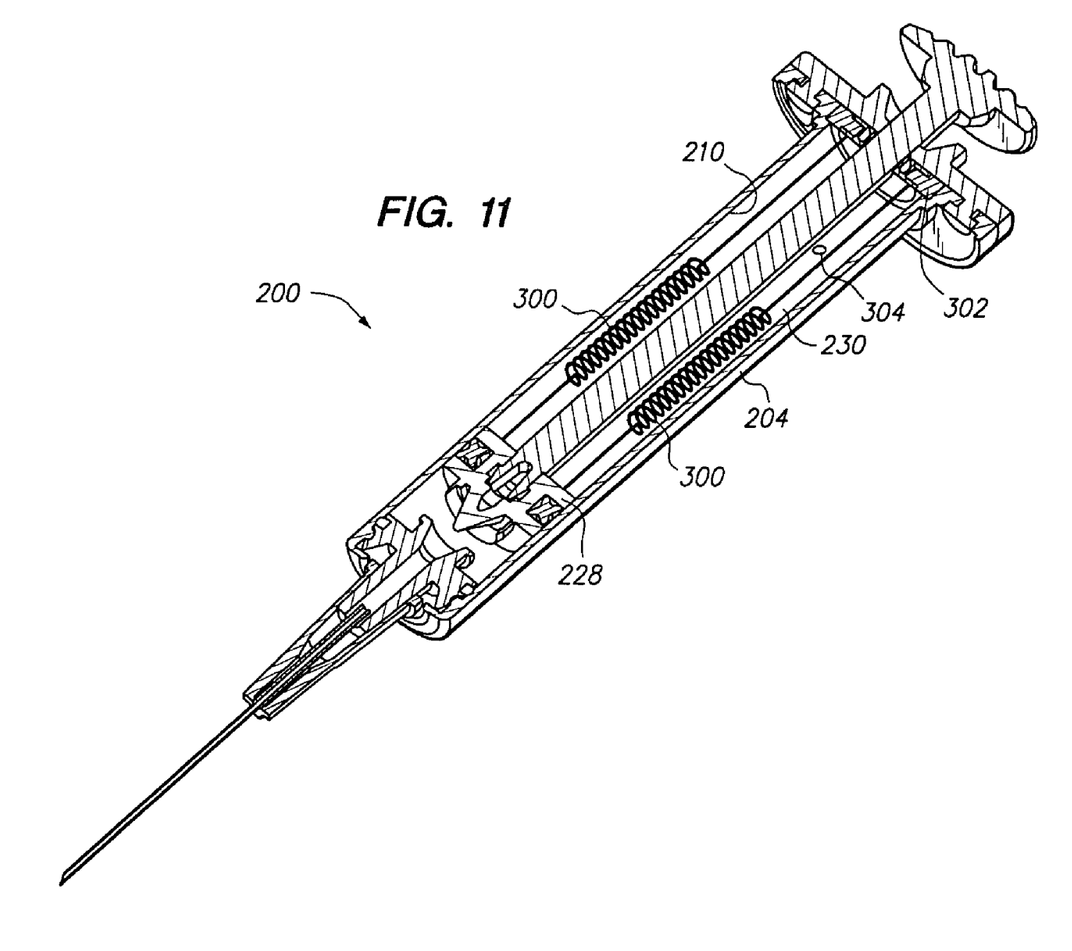
FIG. 11 is an enlarged cross sectional perspective view of the third embodiment of the safety syringe with a tension spring creating a retraction force urging piston toward a retracted position when the piston is traversed toward an extended position or a fully extended position.

The safety syringe 200 shown in FIG. 11 may have at least one but preferably an even number of tension springs 300 (e.g., two) attached to the attachment base 302 and the piston 228. The tension springs 300 may be a helical spring made for tension or an elastic material or other tension spring 300 known in the art. When the piston 228 is in the retracted position, the tension springs 300 may be relaxed in that the tension springs 300 do not urge the piston 228 toward the proximal end of the body 204. In contrast, when the piston 228 is in the extended position (first extended position) or the fully extended position (second extended position), the tension springs 300 may be placed in tension so as to urge the piston 228 toward the proximal end of the body 204 thereby inducing the retraction force. The tension springs 300 may produce an increasing retraction force which urges the piston 228 toward the retracted position or the proximal end of the body 204 as the piston 228 is traversed toward the extended position (first extended position) or the fully extended position (second extended position).

Also, the body 204 of the syringe 200 may have an optional air vent 304 such that air may be introduced into or escape out of a cavity via the air vent 304. The cavity was previously identified as the variable vacuum compartment 230. Such cavity no longer creates a vacuum when the piston 228 is traversed toward the extended position (first extended position) or the fully extended position (second extended position) because air molecules are introduced into the cavity to equalize the pressure within the cavity to the ambient pressure as the piston 228 is traversed to the extended position (first extended position) or the fully extended position (second extended position). Moreover, when the piston 228 is traversed toward the retracted position, air molecules within the cavity escape out of the cavity via the air vent 304 such that pressure is not created within the cavity. Accordingly, when the air vent 304 is formed through the body 204 of the syringe 200, then the retraction force is solely created by the tension springs. Conversely, when the air vent 304 is not formed through the body 204 of the syringe 200, then the retraction force is created by both the tension springs 300 and the variable vacuum compartment 230. Accordingly, the tension springs 300 may replace or be in addition to the variable vacuum compartment 42, 176, 230 discussed above.

The above description is given by way of example, not limitation. Given the above disclosure, one skilled in the art could devise variations that are within the scope and spirit of the invention disclosed herein. Further, the various features of the embodiment disclosed herein can be used alone, or in varying combinations with each other and are not intended to be limited to the specific combination described herein. Thus, the scope of the claims is not to be limited by the illustrated embodiments.

What is claimed is:

1. A retractable safety syringe, comprising:
   a syringe body defining a distal portion, a proximal portion and an inner surface, a detent formed on the inner surface;
   a plunger having a piston slideably disposed within the syringe body and a shaft extending through the proximal portion, the piston having a protuberance extending toward the distal portion of the syringe body,
   a distal seal disposed between the plunger piston and the syringe body forming a fluid tight seal between the plunger piston and the syringe body; and
   a needle holder engageable to the piston, the needle holder having a lower undercut groove sized and configured to receive the detent defining a retaining force, the lower undercut groove removeably engaged with the detent removeably fixing the needle holder to the distal portion of the syringe body, the needle holder having a cavity sized to receive the protuberance of the piston;
   wherein a retraction force tending to move the piston toward the proximal portion of the syringe body arises when the piston is traversed toward the distal portion of the syringe body, and wherein the retraction force is greater than the retaining force when the piston is engaged with the needle holder.

2. The syringe of claim 1 wherein the piston has longitudinally offset tabs and a proximal portion of the needle holder is adapted to engage the longitudinally offset tabs.

3. The syringe of claim 2 wherein an annular ring having an annular flange is formed on the needle holder and is engageable to the longitudinal offset tabs.

4. The syringe of claim 3 wherein the longitudinal offset tabs comprise an upper proximal block tab pushing down on the annular flange and a lower distal wedge tab pulling up on the annular flange when the longitudinal offset tabs are engaged to the annular flange for canting a needle to one side of the syringe body when the needle holder and needle are retracted into the syringe body.

5. The syringe of claim 1 further comprising a braking mechanism for stopping travel of the piston within the syringe body until the piston is engaged to the needle holder.

6. The syringe of claim 1 further comprising a proximal seal disposed between the plunger shaft and syringe body forming a fluid tight seal between the plunger shaft and the syringe body, and wherein the proximal seal and the distal seal form a variable vacuum compartment which creates the retraction force.

7. The syringe of claim 1 further comprising a tension member attached to the piston and proximal end of the body, the tension member creating the retraction force.

8. A retractable safety syringe for injecting fluid, comprising:
   a syringe body defining a distal portion and a proximal portion;
   a plunger having a piston slideably disposed within the syringe body and a shaft extending through the proximal portion, a punch extending distally from the piston;
   a distal seal disposed between the plunger piston and the syringe body forming a fluid tight seal between the plunger piston and the syringe body;
   a needle holder disposable at the distal portion of the syringe body, the needle holder being removeably engageable to the distal portion of the syringe body and engageable to the piston; and
   a release element, distinct from the needle holder and the syringe body and disposed between the needle holder and the syringe body, the release element configured to removeably engage the needle holder to the distal end of the syringe body, the release element traverseable from an engagement position to a release position, the release element at the engagement position holding the needle holder in position relative to the syringe body, the release element at the release position permitting the needle holder to be withdrawn into the syringe body when the piston is engaged to the needle holder, the release element configured to be traversed to the release position by the punch.

9. The syringe of claim 8 wherein the piston has longitudinally offset tabs and a proximal portion of the needle holder is adapted to engage the longitudinally offset tabs.

10. The syringe of claim 9 wherein the needle holder has an annular flange and is engageable to the longitudinal offset tabs.

11. The syringe of claim 10 wherein the longitudinal offset tabs comprise an upper proximal block tab pushing down on the annular flange and a lower distal wedge tab pulling up on the annular flange when the longitudinal offset tabs are engaged to the annular flange for canting a needle to one side of the syringe body when the needle holder and needle are retracted into the syringe body.

12. The syringe of claim 8 further comprising a braking mechanism for stopping travel of the piston within the syringe body until the piston is engaged to the needle holder.

13. The syringe of claim 8 wherein the release element defines internal and external friction surfaces, the internal friction surface frictionally engaged to the needle holder, the external friction surface frictionally engaged to the syringe body.

14. The syringe of claim 13 wherein the release element has an annular configuration.

15. A method of operating a syringe, the syringe comprising a syringe body defining a distal portion and a proximal portion; a plunger having a piston slideably disposed within the syringe body; a needle holder disposable at the distal portion of the syringe body, the needle holder being removeably engageable to the distal portion of the syringe body and engageable to the piston; a release element disposed between the needle holder and the syringe body, the release element removeably engaging the needle holder to the distal portion of the syringe body, and a punch extending distally from the piston, the method comprising:
   filling the syringe body with fluid;
   ejecting the fluid in the syringe body through a needle of the syringe;
   displacing the release element in a direction from the proximal portion to the distal portion of the syringe body using the punch, the displacement disengaging the needle holder from the syringe body;
   engaging the piston to the needle holder; and
   retracting the needle holder into the syringe body.

16. The method of claim 15 wherein the displacing further comprises frictionally sliding the release element against the needle holder and the syringe body in a direction from the proximal portion to the distal portion of the syringe body.

17. The method of claim 15 further comprising:
   resisting a retraction force which urges the piston in a direction from the distal portion to the proximal portion of the syringe body with a retaining force defined by frictional engagement of the release element with the needle holder and the syringe body to hold the needle holder in position while injecting fluid.

18. The syringe of claim 1 wherein the cavity of the needle holder is configured to snugly fit the protuberance of the piston.

19. The syringe of claim 1, further comprising:
a needle seal disposed between the needle holder and the syringe body.

20. The syringe of claim 19, wherein the needle seal is an O-ring.

21. The syringe of claim 19, wherein the needle seal is disposed proximal to the detent.

22. The syringe of claim 1, wherein the protuberance is configured to allow the needle holder to rotate away from a longitudinal axis of the syringe body when the needle holder is engaged with the piston.

23. The syringe of claim 22, wherein the protuberance is flexible.

24. The syringe of claim 22, wherein the protuberance has a conical shape.

25. The syringe of claim 8, wherein:
the piston has a protuberance extending toward the distal portion of the syringe body;
and
the needle holder has a cavity sized to receive the protuberance.

26. The syringe of claim 1, wherein the protuberance is configured to allow the needle holder to rotate away from a longitudinal axis of the syringe body when the needle holder is engaged with the piston.

27. The syringe of claim 26, wherein the protuberance is flexible.

28. The syringe of claim 26, wherein the protuberance has a conical shape.

* * * * *